United States Patent [19]

Cummins et al.

[11] Patent Number: 5,801,226

[45] Date of Patent: Sep. 1, 1998

[54] ORAL CARE COMPOSITIONS

[75] Inventors: Diane Cummins, West Kirby; Karen Marie Pickup, Spital, both of Great Britain; Larry A. Tabak, Rochester, N.Y.

[73] Assignee: Unilever Patent Holdings B.V., Rotterdam, Netherlands

[21] Appl. No.: 628,412

[22] Filed: Apr. 5, 1996

[30] Foreign Application Priority Data

Apr. 5, 1995 [EP] European Pat. Off. ............ 95302271

[51] Int. Cl.$^6$ .................................... C07K 16/00
[52] U.S. Cl. .................... 530/388.2; 530/391.7; 424/141.1; 424/152.1; 424/156.1; 424/181.1
[58] Field of Search .................. 530/388.2, 391.7; 424/141.1, 152.1, 156.1, 181.1

[56] References Cited

PUBLICATIONS

Gibbons (*J. Dent. Res.*, vol. 68, No. 5, pp. 750–760, May 1989). Abstract Only.

Hajishengallis et al., *Infect. Immun.*, vol. 60, No. 12, pp. 5057–5064, 1992. Abstract Only.

*Primary Examiner*—Toni R. Scheiner
*Attorney, Agent, or Firm*—Pillsbury Madison & Sutro LLP

[57] ABSTRACT

The present invention relates to novel monoclonal antibodies, raised against salivary pellicle, which are capable of recognising cryptitopes. They can be conjugated with a therapeutic or cosmetic active agent and can be targeted to the enamel pellicle or to the salivary coat on a developing biofilm on the teeth. They are particularly suitable for inclusion in oral care products.

10 Claims, 2 Drawing Sheets

ORAL CARE COMPOSITIONS

FIELD OF THE INVENTION

The present invention relates to the delivery of therapeutic, eg. antimicrobial, or cosmetic, eg. anti-stain active agents to the tooth surface by the use of antibodies which specifically recognise protein structures (cryptitopes) on a pellicle, and to oral care compositions comprising such antibody systems as hereinafter described in more detail.

BACKGROUND OF THE INVENTION

The acquired enamel pellicle is formed by the selective adsorption of salivary proteins onto a clean tooth surface (Bennick et al. (1979) Biochem. J. 183, 115–126; Bennick et al. (1983) Arch. Oral Biol. 28, 19–27; Rolla et al. (1983) Scand. J. Dent. Res. 91, 186–190; Al-Hashimi et al. (1989) Arch. Oral Biol. 34, 289–295).

It is thought that upon adsorption salivary proteins undergo a conformational change which results in the exposure of hidden structures, referred to as "cryptitopes" (Moreno et al. (1991) Biofouling 4, 3–24).

In-vitro studies suggest that several oral microorganisms, including *Actinomyces viscosus* (an organism that preferentially colonises the teeth and has been associated with gingivitis) have the ability to recognise such cryptitopes and in doing so bind efficiently to enamel resulting in microbial adhesion (Gibbons et al. (1990) Arch. Oral Biol. 35 (suppl.) 1075–1145). Plaque development frequently follows microbial adhesion which in the absence of good oral hygiene often results in a disease state, eg. caries, gingivitis. Certain oral organisms, eg. *A. Viscosus, S. gordonii*, have been shown to bind avidly to proline-rich proteins (PRPs) on hydroxyapatite surfaces but not to PRPs in solution (Gibbons et al. (1988) Infect. Immun. 56, 439–445; Gibbons R. J. (1989) J. Dent. Res. 68, 750–760). Also, studies on FTIR spectra of PRPs in solution and in an adsorbed state have shown marked changes in FTIR spectra consistent with significant changes in beta-sheet and beta-turn contents of adsorbed proteins (Moreno et al. (1991) Biofouling 4, 3–24). The results of these studies suggest but do not confirm the cryptitope theory whereby proteins undergo a conformational change and new sites are exposed upon adsorption to a surface. Furthermore, it is not known whether changes in conformation or cryptitope expression on oral surfaces will provide new immunological targets or epitopes.

Statement of Invention

The present invention relates to the use of monoclonal antibodies (murine) which exclusively recognise the surface bound form of a given pellicular constituent (cryptitope) on the acquired enamel pellicle. Such antibodies, which have been raised against a salivary pellicle, can be used to target "actives" to the pellicle.

The only other antibodies which have been shown to recognise protein on a salivary pellicle are anti-idiotype monoclonal antibodies that have been raised against presumptive adhesins of *S.sanguis*. Results here have shown the ability of the antibodies to mimic an *S.sanguis* adhesin with high specificity and to bind to an epitope that is a receptor for the *S.sanguis* adhesin on a salivary pellicle (Gong et al. (1993) J. Dent. Res. 72, Abs. 1766). However, these antibodies differ from those of the present invention in that they have not been raised against cryptitopes and it is not known if they do indeed recognise cryptitopes on a salivary pellicle.

Other research in this area includes the use of a novel genetically engineered binding protein which competes with a bacterial adhesin for a pellicle binding site. Here a pellicle is allowed to form and then sites are recognised by certain oral bacteria covered with the binding protein (WO-A-92/06192). This binding protein, however, has been engineered based on a particular amino acid sequence region of a salivary protein (PRP) in solution and not on a surface and would have thus not been conformational in structure.

Data that show the binding of human salivary components to oral strains of streptococcal bacteria (eg. Douglas et al., Archs. Oral Biol. 29, 751–757 (1984); Newman et al. (1993) Electrophoresis 14, 1322–1327; Newman et al. (1994) J. Dent. Res. 73, Abst. No. 396) suggest the presence of a salivary "pellicle" over bacterial surfaces within a biofilm.

Surprisingly, it has been found that the antibodies according to the present invention, in addition to recognising cryptitopes on model tooth surfaces, also recognise the same cryptitopes on bacterial pellicles. These antibodies are thus ideal tools to target actives to not only the acquired enamel pellicle but also to a salivary coat on a developing biofilm.

One of the major technical problems associated with the development of effective active systems for oral care benefits is obtaining substantive delivery of the agents to the desired site, eg. tooth where plaque formation occurs. Anti-plaque agents which are currently used are substantive where they bind to oral surfaces via (i) electrostatic (ii) hydrophobic interactions. However, binding which is reversible is non-specific i.e. agents will bind to all oral tissues.

The antibodies of the present invention can be used to target agents (eg. therapeutic, cosmetic) to a site which can serve as an anchor point within the mouth and thereby provide the necessary substantivity for maximum effect.

Although antibodies which have been raised against various oral bacteria eg. *S.mutans, S.sanguis* can be used to target anti-microbials to the bacterial surface in an attempt to break down plaque, the pellicle antibodies of the present invention differ from these antibodies in that in addition to their reactivity against a salivary coat on a developing biofilm where they can target actives to break-down plaque, they can also target actives to a clean tooth surface where they can prevent the build-up of plaque. Also, these antibodies can target a tooth whitening agent (or an agent which breaks down stain) to the site of extrinsic stain formation i.e. the acquired enamel pellicle.

Conjugates can be formed between the monoclonal antibodies of this invention and several active compounds including enzymes, peptides, antibodies, particulate systems, ligands, etc. These compounds can so be targeted to salivary pellicle on the tooth surface to control eg. plaque development, stain formation. Targeting and thus substantivity can lead to a reduced amount of "active" required. The conjugates can be formed chemically or through the tools of molecular biology.

BRIEF DESCRIPTION OF THE INVENTION

DETAILED DESCRIPTION OF THE INVENTION

Figure 1:
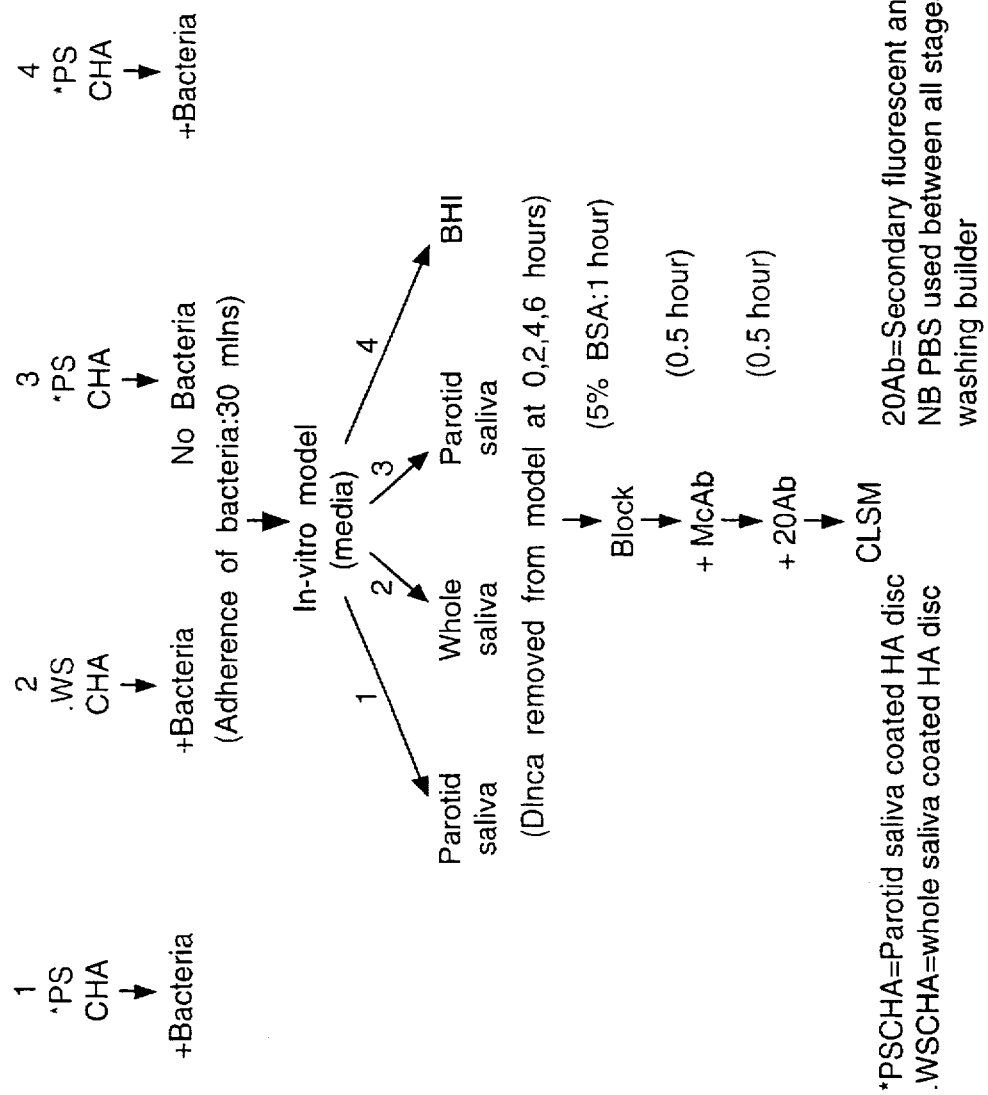
FIG. 1 illustrates the protocol for binding of monoclonal anti-pellicle antibodies to salivary pellicle in vitro.
Figure 2:
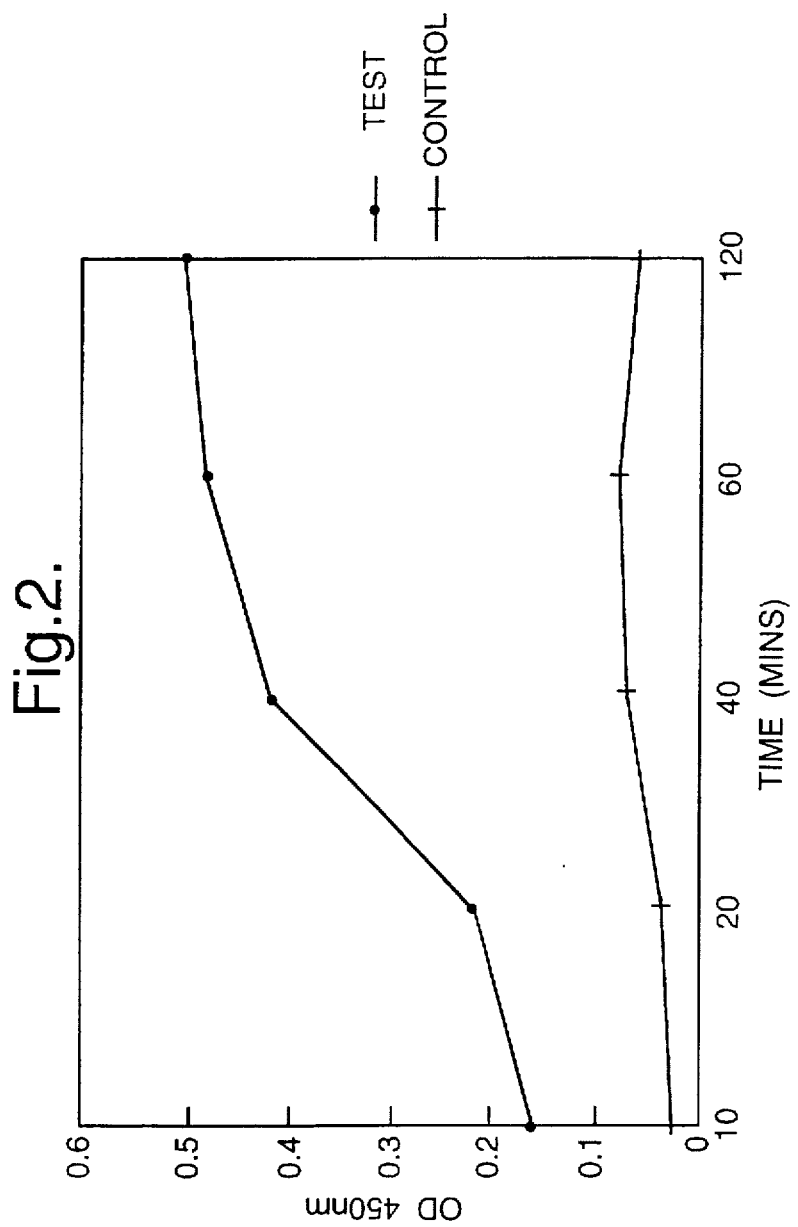
FIG. 2 represents in vitro targeting of oxidative enzymes to a surface by anti-pellicle antibodies.

The purpose of the present invention is to use the monoclonal antibodies of the invention as targeting groups for the substantive delivery of oral care active agents, particularly antimicrobial and anti-stain actives, to the salivary pellicle on tooth and to the salivary coat on bacterial surfaces.

A first antibody or antibody fragment binds to a target site and one or more further antibodies or fragments collectively attach an agent to the target site. Conjugates are formed through either (i) chemical conjugation between pellicle antibodies (fragments) and an agent or (ii) recombinant DNA technology. Alternatively, a fusion can be made which consists of the antibody fragment binding region and the "active".

Finally, conjugates can be formed through non-covalent self assembly systems whereby (i) an anti-pellicle antibody or fragment thereof targets to the desired site and an other antibody (or fragment) system targets to the anti-pellicle antibody or (ii) hybrid antibodies or fragments target to pellicle and "pull down" an anti-microbial enzyme or other active compound (for example bispecific fragments with anti-pellicle and anti-glucose oxidase specifity).

The monoclonal antibodies can be raised against salivary pellicles that are formed from parotid, submandibular/ sublingual and whole saliva.

An advantage of this invention is that pellicle antibodies which have been raised against a parotid saliva pellicle recognise their target in both parotid and whole saliva in-vitro formed pellicles. Another advantage is that such antibodies are substantive (i.e. withstand the flow of saliva), are not inhibited by soluble salivary components and remain reactive vs. their target in the presence of a developing biofilm. Another advantage is that such antibodies are reactive vs. an in-vivo formed pellicle. Such antibodies are ideal tools for targeting "actives" to the tooth surface. Such actives can be targeted to both a clean tooth surface i.e. the acquired enamel pellicle to prevent plaque or stain formation, or to a salivary coat on a developing bacterial biofilm to break-down plaque or stain formation.

Actives that can be used include:
  (i) Antimicrobial:
    (a) antimicrobial enzymes for examples oxidases including glucose oxidase, lactate oxidase, galactose oxidase, uric acid oxidase; peroxidases including horse radish peroxidase, myeloperoxidase, lactoperoxidase, chloroperoxidase; proteases including papain, pepsin, trypsin, ficin, bromelin; cell wall lytic enzymes including lysozyme; specific enzyme inhibitors such as those which inhibit neuraminidase activity or production; plaque matrix inhibitors including dextranases, mutanases.
    (b) antimicrobial peptides for example peptides including bacteriocins, histatins, defensins, cecropins.
    (c) Sequestering agents for example iron sequestering lactoferrin.
  (ii) Cosmetic benefits-producing actives
    (a) Tooth whitening agents for example bleaching enzymes including glucose oxidase, myeloperoxidase; enzymes that break-down stain including proteases.
    (b) anti-malodour compounds including zinc and metal ion complexes.
  (iii) Alkali generating systems including urease, arginine, deaminase, asparginase, etc.
  (iv) Particulate systems including zinc oxide, latex, capsules, liposomes, emulsions.
  (v) Redox buffers Preferred systems include targeted enzymes (enzyme substrates in gels): targeted enzymes in rinse (substrates in gels); targeted enzymes and substrates in rinse; targeted enzymes and substrates in pastes; targeted enzyme and substrates in lozenges.

The recommended concentration of the targeted active-agent/antibody in a product will be from 0.01 µg/g to 50 mg/ml.

The oral compositions can be formulated in any suitable application form, such as emulsions, gels, mouthwashes, toothpowders and toothpastes. They may be formulated into a single formulation or they may be formulated for multi compartment containers into different formulations.

The oral care compositions may, furthermore, comprise optional, conventional ingredients such as pharmaceutically acceptable carriers like starch, sucrose, water or water/alcohol systems etc.. Small amounts of surfactants may also be included, such as anionic, nonionic and amphoteric surfactants. When formulated into a dentifrice, such formulation may contain all the usual dentifrice ingredients.

Thus, they may comprise particulate abrasive materials including agglomerated particulate abrasive materials such as silicas, aluminas, calcium carbonates, dicalciumphosphates, calcium pyrophosphates, hydroxyapatites, trimetaphosphates, insoluble hexametaphosphates and so on, usually in amounts between 5 and 60% by weight.

Furthermore, the dentifrice formulations may comprise humectants such as glycerol, sorbitol, propyleneglycol, polyethyleneglycol, xylitol, lactitol and so on.

Binders and thickeners such as sodium carboxymethylcellulose, xanthan gum, gum arabic etc. may also be included, as well as synthetic polymers such as polyacrylates and carboxyvinyl polymers such as Carbopol®.

Flavours such as peppermint and spearmint oils may also be included, as well as preservatives, opacifying agents, colouring agents, pH-adjusting agents, sweetening agents and so on.

Anti-bacterial agents may also be included such as Triclosan, chlorhexidine, copper-, zinc- and stannous salts such as zinc citrate, sodium zinc citrate and stannous pyrophosphate, sanguinarine extract, metronidazole. Further examples of additional anti-bacterial agents are quaternary ammonium compounds such as cetylpyridinium chloride; bis-guanides such as chlorhexidine digluconate, hexetidine, octenidine, alexidine; halogenated bisphenolic compounds such as 2,2' methylenebis-(4-chloro-6-bromophenol).

Polymeric compounds which can enhance the delivery of active ingredients such as anti-bacterial agents can also be included. Examples of such polymers are copolymers of polyvinylmethylether with maleic anhydride and other similar delivery enhancing polymers, e.g. those described in DE-A-3,942,643 (Colgate).

Furthermore anti-inflammatory agents such as ibuprofen, flurbiprofen, aspirin, indomethacin etc. may also be included.

Anti-caries agents such as sodium- and stannous fluoride, aminefluorides, monosodiumfluorophosphate, casein, plaque buffers such as urea, calcium lactate, calcium glycerophosphate, strontium polyacrylates may also be included. Other optional ingredients include vitamins such as Vitamin C, and plant extracts. Desensitising agents such as potassium citrate, potassium chloride, potassium tartrate, potassium bicarbonate, potassium oxalate, potassium nitrate as well as strontium salts may also be included.

Buffers and salts to buffer the pH and ionic strength of the compositions may also be included. Liposomes and other encapsulates may also be used to improve delivery or stability of active ingredients.

Furthermore, the oral compositions may comprise anti-calculus agents such as alkalimetal pyrophosphates, hypophosphite-containing polymers, organic phosphonates, phosphocitrates etc.

In addition, the compositions may comprise further functional biomolecules such as bacteriocins, antibodies, enzymes and so on.

Other optional ingredients that may be included are e.g. bleaching agents, e.g. those described in EP-A-0 545,594, organic peroxyacids, effervescing systems such as sodium bicarbonate/citric acid systems, colour change systems, and so on.

When formulated as a mouthwash, the oral care composition usually comprises a water/alcohol solution, flavour, humectant, sweetener and colorant.

The present invention will further be illustrated by way of Example.

EXAMPLE 1

Generation of Cryptitope—Specific Monoclonal Antibodies

Method

1) Immunisation

Immunogen—One ml of freshly collected parotid saliva was added to 35 mg of pre-washed (washed with phosphate buffered saline: PBS pH 7.4) hydroxyapatitie (HA) for two hours at 4° C. with end over end mixing. Parotid saliva coated HA was then washed (PBS) and centrifuged X2 (2000 g). The resultant pellet was mixed with either Freund's adjuvant or Titre adjuvant to increase the immune response prior to administration of the vaccine to mice (day 1). Mice were re-injected with the above immunogen on day 8. The immune response of the mice was boosted on days 15, 22, 30 by injection of parotid saliva coated HA. A fusion was performed on day 35.

Cell fusion—The spleen from an immunised mouse was removed and placed in 30 ml of serum free RPMI 1640 media to form a single cell suspension. The spleen cells were then fused with a myeloma cell line using polyethylene glycol. Cells were then dispersed into HAT (Hypoxanthine, Aminopterin, Thymidine)media (a media that is used to promote conditions which allows the growth of hybrid cells only) and aliquoted into 96 well tissue plates.

2) Screening Assay—Detection of antibodies with specificity for surface bound determinants on parotid saliva coated HA. PBS washed HA was added to freshly collected parotid saliva at a concentration of 35 mg HA/ml of parotid saliva. The sample was then mixed overnight end over end at 4° C. Following this, the sample was washed (PBS) and centrifuged (2000 g) X2 prior to the addition of 5% Bovine Serum Albumin (BSA) in PBS (PBSA). Saliva coated HA was then mixed end over end for one hour at 4° C. The sample was then washed as above before PBSA was added to the HA pellet to a concentration of 5 mg HA/100 µl PBSA. Following this, 100 µl aliquots of the HA sample were added to Eppendorf tubes. PBSA (150 µl) or fresh parotid saliva (150 µl) was then added to HA prior to the addition of antibody (100 µg/ml).

Samples were incubated at room temperature for a period of 30 minutes and vortexed twice (time 0.15 minutes) during this time. Samples were washed and centrifuged X3 with 500 µl of 0.05% Tween 20 in PBS (PBST). A secondary antibody labelled with Horse Radish Peroxidase (HRP) was then added (250 µl, 1/1000 dilution) for 30 minutes at room temperature (sample was vortexed at time 0 and 15 minutes as above). Following this, the samples were again washed and centrifuged X3 with 500 µl PBST prior to the addition of 250 µl of the substrate TMB (3,3',5,5' Tetramethylbenzidine) (4 minutes, RT). The reaction was stopped via the addition of 2M $H_2SO_4$ (250 µl). Finally, 400 µl of each reaction mixture was filtered and the filtrate transferred to an ELISA plate where readings were taken on a spectrophotometer at an absorbance of $450_{nm}$.

Results

Generation of Cryptitope—Specific Monoclonal Antibodies

Numerous cell lines were screened for antibody production in the above modified ELISA screen. Cell lines that were positive were cloned and then "grown up" to mg quantities in hollow cell fibre reactors.

Table 1 illustrates ELISA results from cloned and gr

* * * * *